US009757064B2

(12) United States Patent
Hsiao et al.

(10) Patent No.: US 9,757,064 B2
(45) Date of Patent: Sep. 12, 2017

(54) WRIST JOINT PERFORMANCE MEASURING DEVICE

(71) Applicant: E-DA HOSPITAL, Kaohsiung (TW)

(72) Inventors: Chih-Kun Hsiao, Kaohsiung (TW);
Yuan-Kun Tu, Kaohsiung (TW);
Yi-Jung Tsai, Kaohsiung (TW);
Teng-Yao Yang, Kaohsiung (TW);
Shang-Hua Yu, Kaohsiung (TW);
Chun-Wei Kang, Kaohsiung (TW);
Hao-Yuan Hsiao, Kaohsiung (TW)

(73) Assignee: E-Da Hospital, Kaohsiung (TW)

( * ) Notice: Subject to any disclaimer, the term of this patent is extended or adjusted under 35 U.S.C. 154(b) by 48 days.

(21) Appl. No.: 14/789,125

(22) Filed: Jul. 1, 2015

(65) Prior Publication Data

US 2017/0000408 A1   Jan. 5, 2017

(51) Int. Cl.
*A61B 5/00* (2006.01)
*A61B 5/11* (2006.01)
*A61B 90/00* (2016.01)

(52) U.S. Cl.
CPC ............ *A61B 5/459* (2013.01); *A61B 5/1121* (2013.01); *A61B 5/70* (2013.01); *A61B 2090/066* (2016.02)

(58) Field of Classification Search
None
See application file for complete search history.

(56) References Cited

U.S. PATENT DOCUMENTS

| | | | |
|---|---|---|---|
| 5,720,711 A | 2/1998 | Bond et al. | |
| 7,618,381 B2 | 11/2009 | Krebs et al. | |
| 2006/0106326 A1 | 5/2006 | Krebs et al. | |
| 2012/0238920 A1* | 9/2012 | Schnapp | A61H 1/0285 601/5 |
| 2013/0012362 A1* | 1/2013 | Ju | A61H 1/0285 482/49 |

* cited by examiner

*Primary Examiner* — Devin Henson
*Assistant Examiner* — Benjamin Melhus
(74) *Attorney, Agent, or Firm* — Alan D. Kamrath; Kamrath IP Lawfirm, P.A.

(57) ABSTRACT

A wrist joint performance measuring device includes a base having a seat and two positioning arms on two sides of the seat. A switching device is pivotably mounted to the base. A forearm support is connected to the switching device. A measurement device includes a pivotal seat, a torque meter, a first handle, and a second handle. The pivotal seat is pivotably connected to the forearm support. The torque meter is mounted to the pivotal seat. The first handle or the second handle is connected to a force receiving end of the torque meter. The forearm support and the measurement device are movable by the switching device to one of the two positioning arms and are positioned by the one of the two positioning arms.

19 Claims, 14 Drawing Sheets

WRIST JOINT PERFORMANCE MEASURING DEVICE

BACKGROUND OF THE INVENTION

1. Field of the Invention

The present invention relates to a wrist joint performance measuring device and, more particularly, to a wrist joint performance measuring device for measuring the torque and the movement angle of a wrist joint.

2. Description of the Related Art

FIG. 1 shows a conventional wrist joint performance measuring device 9 including a base 91 and a pivotal measurement table 92. The pivotal measurement table 92 includes an operation face 921. The pivotal measurement table 92 is pivotable relative to the base 91, such that the operation face 921 can face upwards or forwards in relation to the base 91. The conventional wrist joint performance measuring device 9 further includes a measurement module 93 having an immobile member 931, a rotational member 932, and a torque sensor. The immobile member 931 is fixed to and protrudes from the operation face 921. The rotational member 932 rotatably protrudes out of the operation face 921. The torque sensor is mounted in the base 91 and is indirectly connected to the rotational member 932 for measuring the torque of the rotational member 932. An example of such a conventional wrist joint performance measuring device 9 is disclosed in U.S. Pat. No. 5,720,711 entitled "PHYSIOLOGICAL EVALUATION AND EXERCISE SYSTEM".

When the operation face 921 of the pivotal measurement table 92 is in a position facing upwards, a testee can stand in front of the base 91 and hooks the immobile member 931 with the web between the thumb and the index finger of the right hand. The testee uses four fingers (except the thumb) to hold the rotational member 932 and applies a force to rotate the rotational member 932 for measuring the flexion torque of the wrist joint of the right hand. Alternatively, the user can abut the rotational member 932 with the back of the four fingers and apply a force to rotate the rotational member 932 for measuring the extension torque of the wrist joint of the right hand. When the testee intends to test the left hand, the testee must move a small distance to a position on the front left side of the base 91, such that the testee can proceed with measurement of the flexion torque and the extension torque of the wrist joint of the left hand.

On the other hand, with reference to FIG. 2, when the operation face 921 of the pivotal measurement table 92 is in a position facing forwards, the immobile member 931 can be detached, the rotational member 932 can be replaced by a handle 933. The testee can sit in a chair on the front right side of the base 91, can hold the handle 933 with the right hand, and can apply a force to move the handle 933 in the counterclockwise direction or the clockwise direction for measuring the pronation torque or the supination torque of the wrist joint of the right hand. When it is desired to test the left hand, the testee must stand up and move the chair through a small distance to a position on the front left side of the base 91 for proceeding with measurement of the pronation torque or the supination torque of the wrist joint of the left hand.

However, during use of the conventional wrist joint performance measuring device 9, the upper limb, particularly the forearm, of the testee is not restrained, such that the testee cannot easily control the force to be applied by the wrist only, and the measurement result is often the combination of the forces resulting from cooperation of many joints and muscles of the upper limb, leading to inaccurate measurement results.

Furthermore, in use of the conventional wrist joint performance measuring device 9, the testee has to change the postures (standing or sitting) according to the test items and has to change the position to accommodate the conventional wrist joint performance measuring device 9, which is inconvenient to use. Furthermore, after the body of the testee is moved, it is difficult to ensure the hand of the testee in the best force-applying position, adversely affecting the measurement accuracy.

Thus, improvement to the conventional wrist joint performance measuring device is desired.

SUMMARY OF THE INVENTION

An objective of the present invention is to provide a wrist joint performance measuring device capable of assisting a testee in precisely applying a force from the wrist.

Another objective of the present invention is to provide a wrist joint performance measuring device capable of performing various test items without changing the position of the testee.

The present invention fulfills the above objectives by providing a wrist joint performance measuring device including a base having a seat and two positioning arms on two sides of the seat. A switching device is pivotably mounted to the base. A forearm support is connected to the switching device. A measurement device includes a pivotal seat, a torque meter, a first handle, and a second handle. The pivotal seat is pivotably connected to the forearm support. The torque meter is mounted to the pivotal seat. The first handle or the second handle is connected to a force receiving end of the torque meter. The forearm support and the measurement device are movable by the switching device to one of the two positioning arms and are positioned by the one of the two positioning arms.

The forearm support can include a bottom board and a forearm positioning portion. The bottom board is connected to the switching device. The forearm positioning portion is mounted on top of the bottom board.

The bottom board can include a guiding groove and an extension arm movably received in the guiding groove. An end of the extension arm located outside of the guiding groove has a pivotal portion. The pivotal seat includes a pivotal portion pivotably connected to the pivotal portion of the extension arm.

The extension arm can include two positioning holes. The pivotal seat can include a through-hole and an insert. The through-hole of the pivotal seat is aligned with one of the two positioning holes. The insert extends through the through-hole into one of the two positioning holes.

The switching device can include a first arm and a second arm. The first arm is pivotably mounted to the base. The second arm is directly or indirectly connected to the first arm and is pivotable relative to the first arm. The bottom board is connected to the second arm.

The bottom board can be pivotably connected to the second arm.

The second arm can be translateably connected to the first arm.

The pivotal seat can include a compartment, a clamping member, and a fine adjustment module. The torque meter is clamped by the clamping member. The clamping member is received in the compartment. The fine adjustment module is configured to adjust a position of the clamping member in the compartment.

The clamping member can include a screw hole. The fine adjustment module can include a pressing block, a threaded rod, and a knob. The pressing block is mounted to a side of the pivotal seat. The threaded rod extends through the pivotal seat. A threaded portion of the threaded rod is received in the compartment and threadedly engages with the screw hole of the clamping member. The knob is mounted to an end of the threaded rod outside of the pressing block.

The measurement device can be connected to the force receiving end of the torque meter by a connection member. The first handle is mounted to the connection member. The second handle is detachably mounted to the connection member.

The connection member can include a connection rod. The connection rod has a receiving hole and a rotation preventing hole. The receiving hole and the rotation preventing hole intercommunicate with each other and respectively extend through two ends of the connection rod. The force receiving end of the torque meter is received in the receiving hole of the connection rod. The rotation preventing hole has non-circular cross sections. The second handle is detachably engaged in the rotation preventing hole.

The second handle can include an insertion portion and a gripping portion. The insertion portion is located on an end of the second handle. The insertion portion matches with the rotation preventing hole. The insertion portion of the second handle is inserted into the rotation preventing hole. A longitudinal axis of the gripping portion is orthogonal to a longitudinal axis of the insertion portion.

The connection member can further include an extension rod connected to an outer periphery of the connection rod. The extension rod extends away from the forearm support. The first handle is mounted to the extension rod.

The first handle can include a fixing rod, a follower, a sleeve, an inner rod, and a return spring. An end of the fixing rod has an end fixed to the extension rod. The follower is connected to the other end of the fixing rod. The sleeve is mounted around the follower. The inner rod extends through the follower and includes an end having an arcuate surface abutting an interior of the fixing rod. The other end of the inner rod is received in the sleeve and has a stopper. The return spring is mounted around the inner rod and includes a first end abutting the follower and a second end abutting the stopper.

The measurement device can further include a casing. The torque meter is received in the casing. The torque meter includes a bottom having a rotation prevention hole and a rotation preventing member. The rotation preventing member matches with the rotation prevention hole of the torque meter and has non-circular cross sections.

The casing can include a first casing part and a second casing part coupled with the first casing part. The first casing part includes a hole. The first casing part further includes a stop plate pivotably mounted to an outer periphery of the first casing part. The rotation preventing member extends into the rotation prevention hole. The stop plate blocks the hole to abut an end of the rotation preventing member.

The rotation preventing member can include an outer periphery having a protrusion. The protrusion has a maximum width larger than a maximum diameter of the rotation prevention hole. When the rotation preventing member is moved out of the rotation prevention hole, the rotation preventing member moves through the hole and partially extends out of the first casing part, and the protrusion prevents the rotation preventing member from falling out of the casing.

The second casing part can be mounted to the clamping member. The second casing part can include an engagement hole. The force receiving end of the torque meter extends out of the engagement hole. The connection rod of the connection member is aligned with the engagement hole.

The second casing part can include an outer periphery having a scale. The scale is provided around the engagement hole.

The measurement device can further include a locking seat and two clamping rods. The locking seat is mounted to the second casing part. The locking seat includes a wider groove and a narrower groove intercommunicated with the wider groove. Each of the two clamping rods has an end extending through the narrower groove and threadedly engaged with a nut in the wider groove.

The present invention will become clearer in light of the following detailed description of illustrative embodiments of this invention described in connection with the drawings.

The present invention will become clearer in light of the following detailed description of illustrative embodiments of this invention described in connection with the drawings.

DETAILED DESCRIPTION OF THE INVENTION

Figure 1:
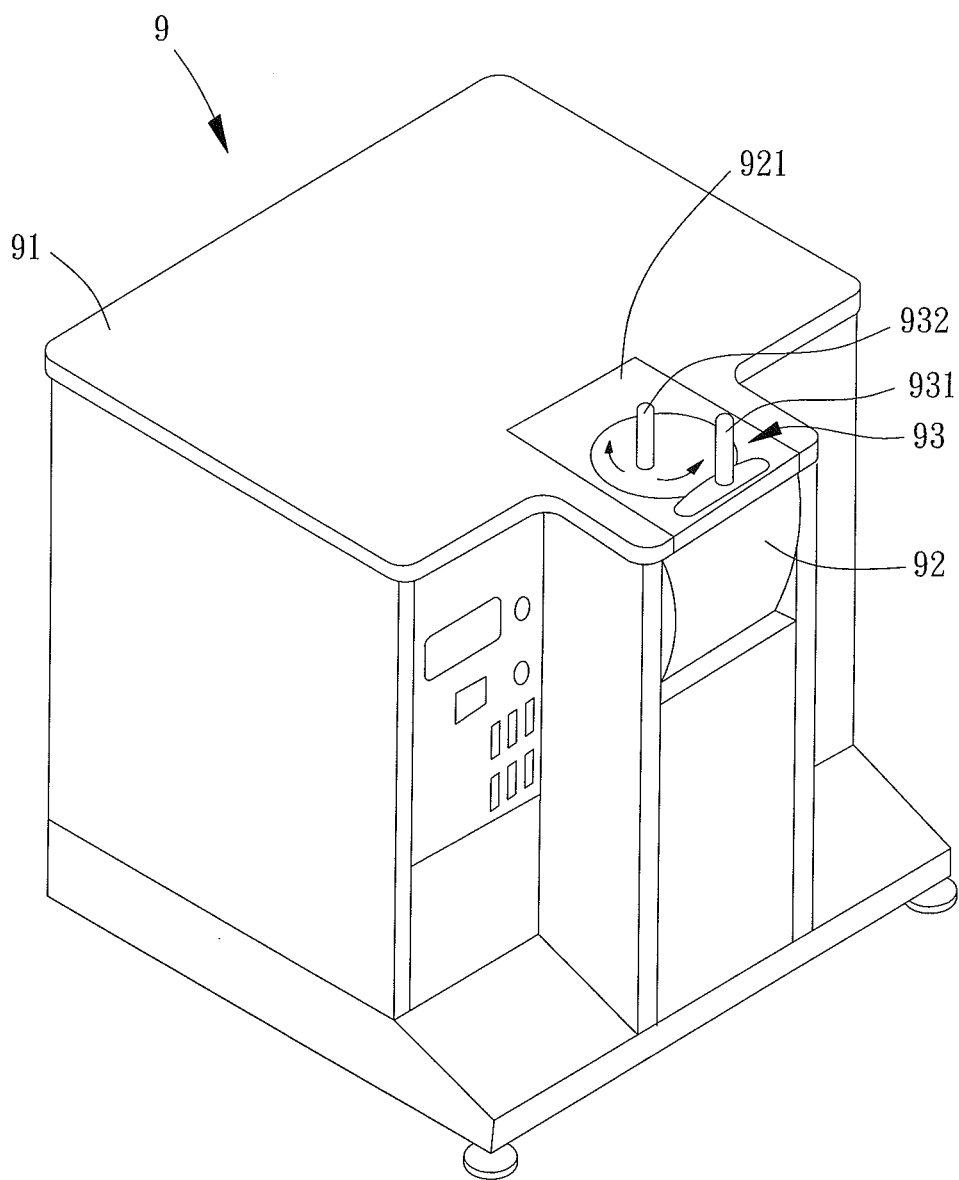
FIG. 1 shows a perspective view of a conventional wrist joint performance measuring device.
Figure 2:
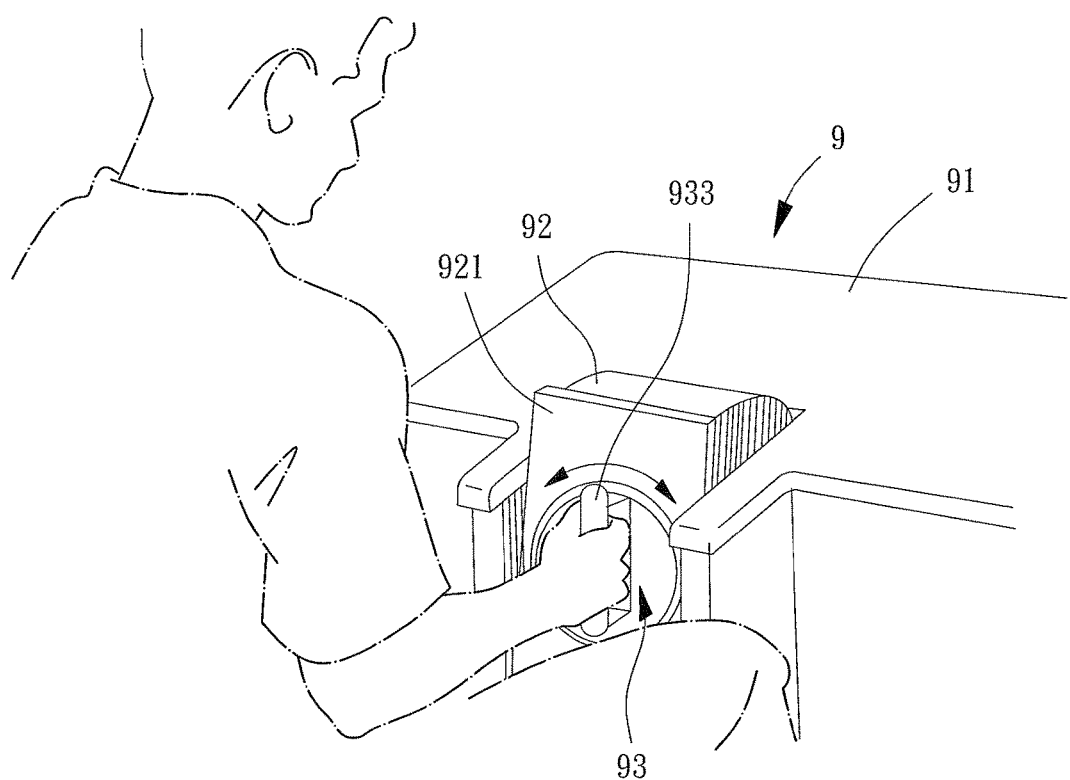
FIG. 2 is a diagrammatic perspective view illustrating use of the conventional wrist joint performance measuring device.
Figure 3:
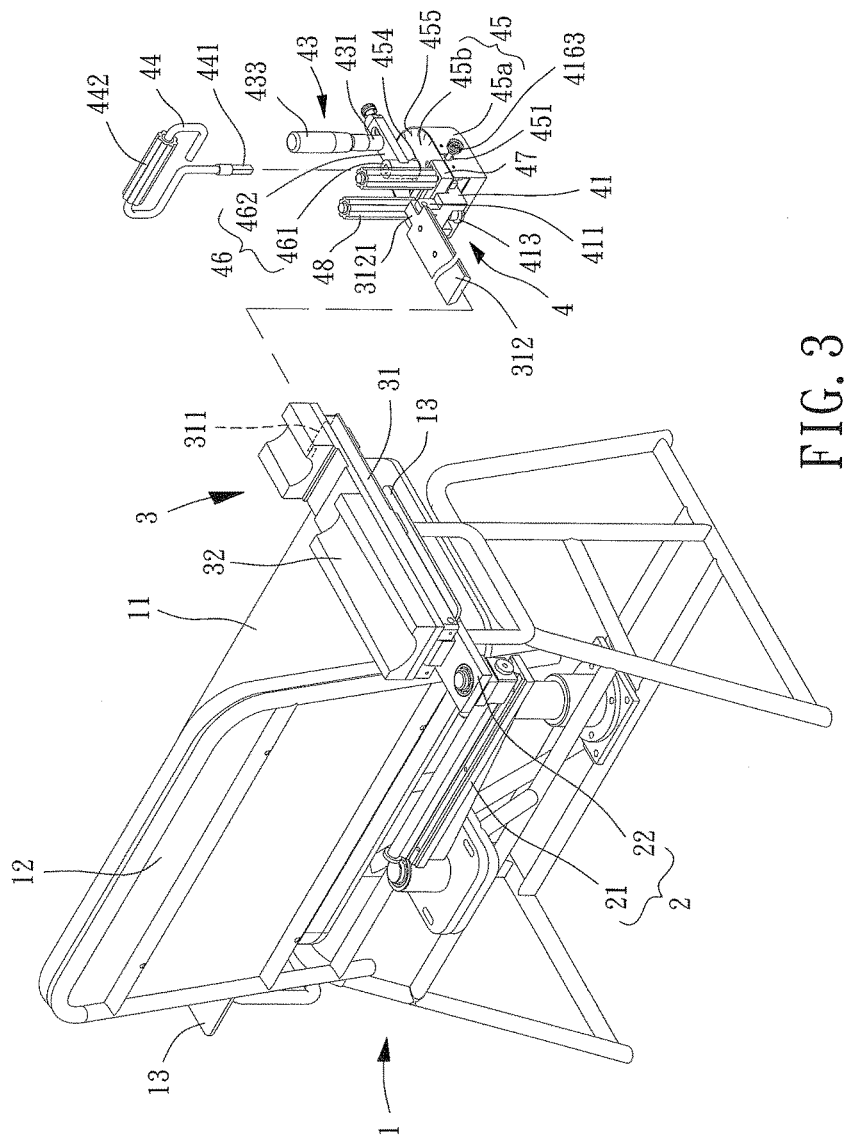
FIG. 3 is a partly-exploded perspective view of a wrist joint performance measuring device of an embodiment according to the present invention.

FIG. 3 shows a wrist joint performance measuring device of an embodiment according to the present invention. The wrist joint performance measuring device includes a base 1, a switching device 2, a forearm support 3, and a measurement device 4. The switching device 2 is pivotably mounted to the base 1. The forearm support 3 is connected to the switching device 2. The measurement device 4 is pivotably mounted to the forearm support 3. The base 1 can support a testee. The switching device 2 can move the forearm support 3 and the measurement device 4 to the left side or the right side of the testee for proceeding with measurement of the wrist joint performance of the left hand or the right hand of the testee.

In this embodiment, the base 1 can be a frame in the form of a chair. The base 1 includes a seat 11, a backrest 12, and two positioning arms 13. The backrest 12 is on the rear end of the seat 11. The testee can sit in the seat 11 with the back of the testee lying on the backrest. The two positioning arms 13 are on the left and right sides of the seat 11. The forearm support 3 and the measurement device 4 can be moved by the switching device 2 to the left or right side of the testee and can be positioned by one of the two positioning arms 13. The height of the seat 11 from the ground, the height difference between the seat 11 and the two positioning arms 13, and the angle of the backrest 12 relative to the seat 11 are preferably adjustable to suit testees of various heights and figures. The structures with the above functions can be conventional.

The switching device 2 includes a plurality of arms pivotably connected to each other. One of the arms at an end of the switching device 2 is pivotably mounted to the base 1. Another arm at the other end of the switching device 2 is connected to the forearm support 3. Thus, the arms provide various degrees of freedom to permit the forearm support 3 to be moved to the left or right side of the testee according to need, and the forearm support 3 can be positioned to one of the two positioning arms 13. Specifically, the switching device 2 can include a first arm 21 and a second arm 22. The first arm 21 is pivotably mounted to the base 1. Preferably, the first arm 21 is pivotably connected to a center of a rear of the backrest 12. The second arm 22 is directly or indirectly connected to the first arm 22 and is pivotable relative to the first arm 21. The pivotal axes of the first arm 21 and the second arm 22 can be parallel to each other. Furthermore, the second arm 22 can be translateably connected to the first arm 21. Thus, after the switching device 2 has been assembled to the seat 1, the connection position between the second arm 22 and the first arm 21 can be adjusted according to the width of the seat 11, assuring the forearm support 3 can be accurately moved by the switching device 2 to the left or right side of the testee.

The forearm support 3 includes a bottom board 31 and a forearm positioning portion 32. The bottom board 31 can be fixed or pivotably connected to the second arm 22. In this embodiment, the bottom board 31 is pivotably connected to the second arm 22. The forearm positioning portion 32 can be mounted on top of the bottom board 31, such that the testee can place a forearm on the forearm positioning portion 32. The forearm positioning portion 32 can be a soft pad. Preferably, the forearm positioning portion 32 has a central recessed portion, such that the testee can place the forearm in the forearm positioning portion 32, and two protrusive sides of the forearm positioning portion 32 can envelope the inner and outer sides of the forearm of the testee to reliably position the forearm. In an alternative embodiment, the forearm positioning portion 32 can be annular. The testee can directly extend the forearm into the forearm positioning portion 32 and then tie the forearm in place, achieving a more reliable positioning effect.

Figure 4:
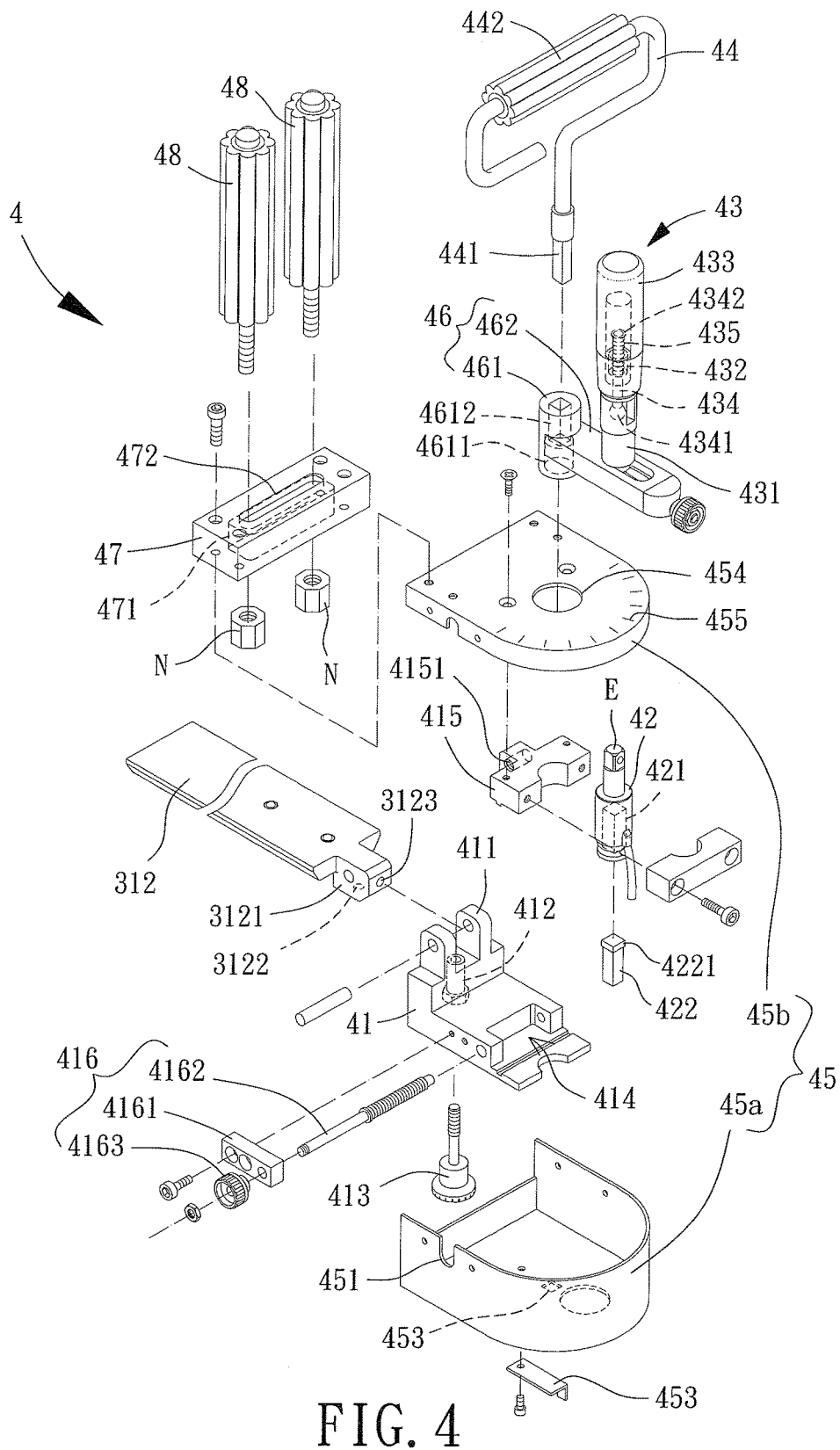
FIG. 4 is an exploded, perspective view of a measurement device of the wrist joint performance measuring device of the embodiment according to the present invention.

The measurement device 4 is pivotably connected to the forearm support 3. Namely, the measurement device 4 can be pivotably connected to the bottom board 31 or the forearm positioning portion 32. In this embodiment, the measurement device 4 is pivotably connected to the bottom board 31. Furthermore, the bottom board 31 can adjust the distance from the measurement device 4 to the forearm positioning portion 32. Specifically, the bottom board 31 can include a guiding groove 311 and an extension arm 312. The guiding groove 311 and the extension arm 312 can match with each other (such as a dovetail groove and a dovetail structure). The extension arm 312 is movably received in the guiding groove 311. An end of the extension arm 312 outside of the guiding groove 311 has a pivotal portion 3121 for pivotal connection with the pivotal seat 41. With reference to FIG. 4, the extension arm 312 includes two positioning holes 3122 and 3123.

With reference to FIGS. 3 and 4, the measurement device 4 includes a pivotal seat 41, a torque meter 42, a first handle 43, and a second handle 44. The pivotal seat 41 is pivotably connected to the forearm support 3. The torque meter 42 is mounted to the pivotal seat 41. A force receiving end "E" of the torque meter 42 is directly or indirectly connected to the first handle 43 or the second handle 44 according to the test item. The measurement device 4 can further include a casing 45 for reliably positioning many elements while protecting the pivotal seat 41 and the torque meter 42 from impact as well as keeping the appearance of the measurement device 4 tidy. In this embodiment, the casing 45 includes a first casing part 45a and a second casing part 45b engaged with the first casing part 45a.

The pivotal seat 41 includes a pivotal portion 411 pivotably connected to the pivotal portion 3121 of the extension arm 32 of the forearm support 3. The pivotal seat 41 includes a through-hole 412 and an insert 413. The pivotal seat 41 can pivot relative to the extension arm 312 to align the pivotal seat 41 with one of the two positioning holes 3122 and 3123. The insert 413 can be a screw or a pin. The insert 413 is movable in the through-hole 412. Thus, the insert 413 can extend through the through-hole 412 into one of the two positioning holes 3122 and 3123 to position the pivotal seat 41 relative to the extension arm 312.

The pivotal seat 41 can further include a compartment 414 and a clamping member 415. The clamping member 415 can be in any desired form for reliably clamping the torque meter 42 and should not be limited to the illustrated embodiment. The clamping member 415 is received in the compartment 414. The position of the clamping member 415 in the compartment 414 can be adjusted by a fine adjustment module 416 for achieving fine adjustment of the position of the torque meter 42. In this embodiment, the clamping member 415 includes a screw hole 4151, and the fine adjustment module 416 includes a pressing block 4161, a threaded rod 4612, and a knob 4163. The pressing block 4161 is mounted to a side of the pivotal seat 41. The threaded rod 4612 extends through the pivotal seat 41. A threaded portion of the threaded rod 4612 is received in the compartment 414 and threadedly engages with the screw hole 4151 of the clamping member 415. The knob 4163 is mounted to an end of the threaded rod 4612 outside of the pressing block 4161. Thus, when the knob 4163 is rotated, the threaded rod 4612 actuates the clamping member 415 to move through a small displacement.

A portion of the pivotal seat 41 including the pivotal seat 411, the through-hole 412, and the insert 413 is exposed outside of the casing 45. Most of the remaining portion of the pivotal seat 41 is received in the casing 45. The casing 45 includes a slot 451 in a side thereof. The end of the threaded rod 4612 extends through the slot 451 and engages with the knob 4163, permitting adjustment of the positions of the clamping member 415 and the torque meter 42 from outside of the casing 45.

Figure 6:
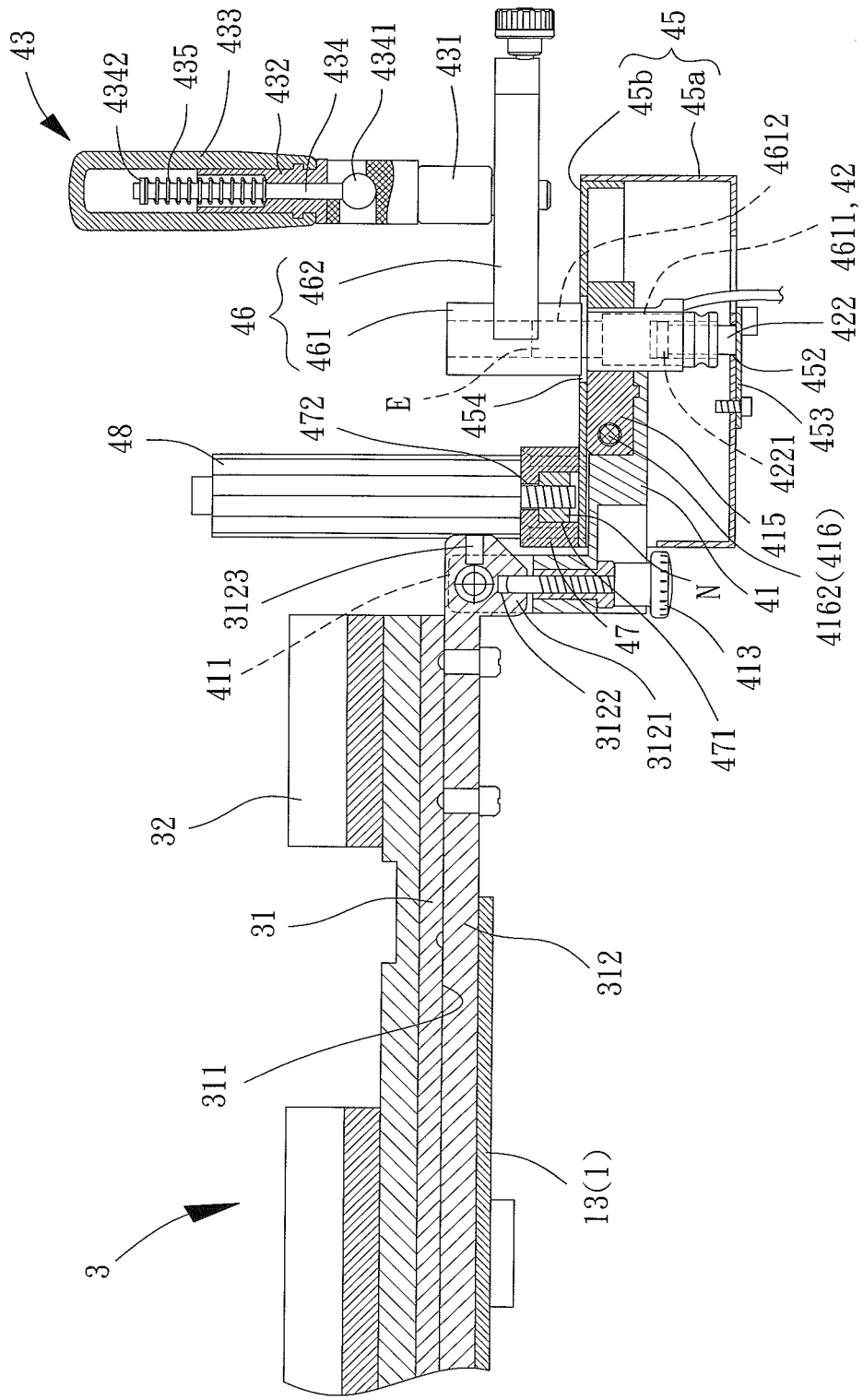
FIG. 6 is a cross sectional view of the wrist joint performance measuring device of the embodiment according to the present invention in a state for measuring the flexion torque or the extension torque of a wrist joint.
Figure 8:
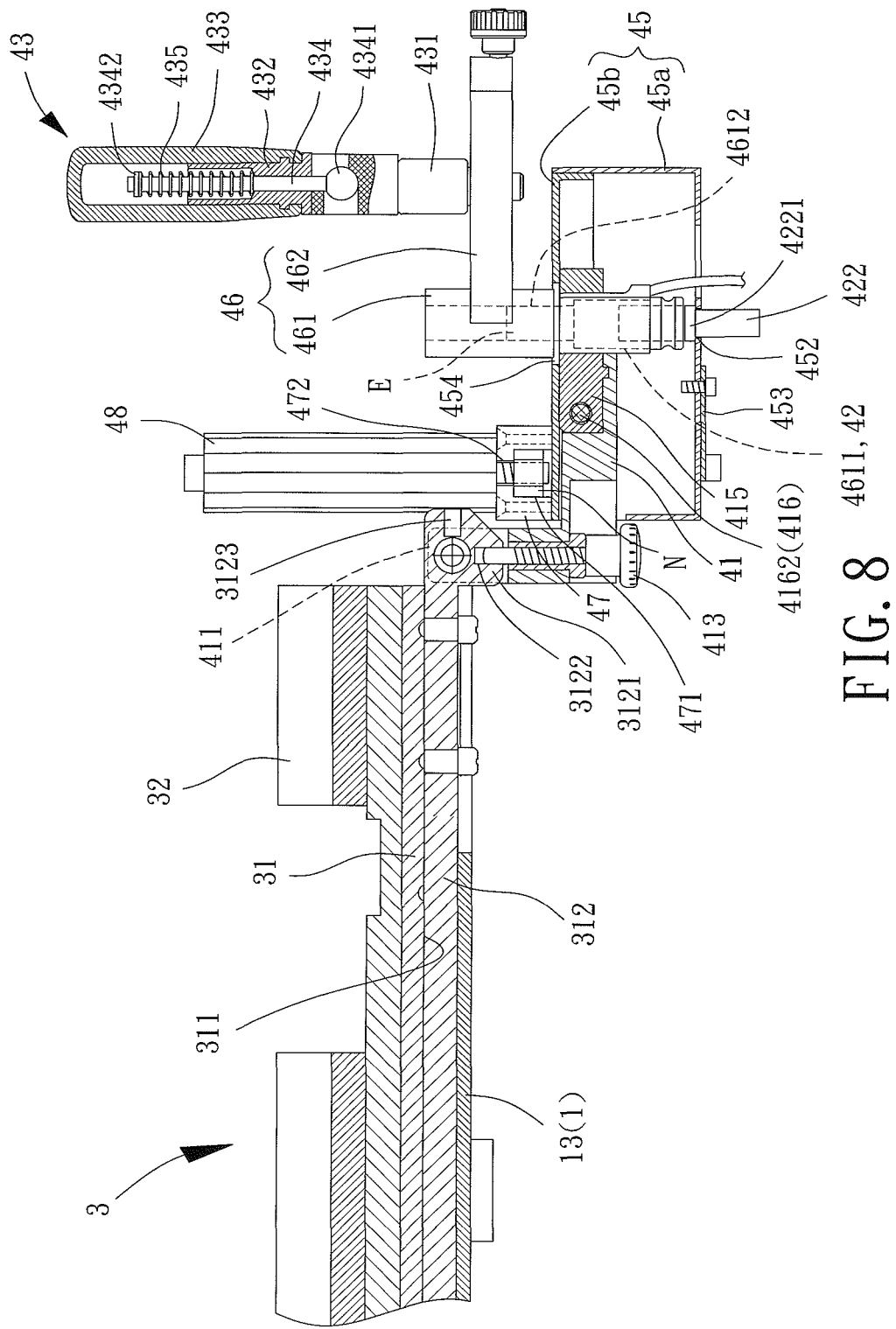
FIG. 8 is a cross sectional view of the wrist joint performance measuring device of the embodiment according to the present invention in a state for measuring the flexion/extension movement angle of a wrist joint.

The torque meter 42 includes a bottom having a rotation prevention hole 421 and a rotation preventing member 422. The rotation preventing member 422 matches with the rotation prevention hole 421 and has non-circular cross sections. Thus, a core of the torque meter 42 cannot rotate when the rotation preventing member 422 extends into the rotation prevention hole 421. For example, the rotation prevention hole 421 can be a blind hole having square cross sections, and the rotation preventing member 422 can be a column having square cross sections. Furthermore, the rotation preventing member 422 includes an outer periphery having a protrusion 4221. The protrusion 4221 has a maximum width larger than a maximum diameter of the rotation prevention hole 421. The first casing part 45a includes a hole 452. The first casing part 45a further includes a pivotable stop plate 453 on an outer periphery thereof. As shown in FIG. 6, the rotation preventing member 422 can extend into the rotation prevention hole 421, and the stop plate 453 blocks the hole 452 to abut an end of the rotation preventing member 422. On the other hand, as shown in FIG. 8, the stop plate 453 can be pivoted to a position not abutting the rotation preventing member 422, such that the rotation preventing member 422 can be moved out of the rotation prevention hole 421. The rotation preventing member 422 moves through the hole 452 and partially extends out of the first casing part 45a, and the protrusion 4221 prevents the rotation preventing member 422 from falling out of the casing 45.

With reference to FIGS. 3 and 4, the second casing part 45b includes an engagement hole 454. Furthermore, the second casing part 45b includes an outer periphery having a scale 455 provided around the engagement hole 454. The scale 455 includes angle indicating marks. The second casing part 45b is mounted to the clamping member 415 with the force receiving end "E" of the torque meter 42 extending out of the engagement hole 454. To increase use convenience, in this embodiment, a connection member 46 is connected to the force receiving end "E" of the torque meter 42. Then, the first handle 43 is mounted to the connection member 46, and the second handle 44 is detachably mounted to the connection member 46. Thus, the force applied to the first handle 43 or the second handle 44 can be transmitted through the connection member 46 to the torque meter 42.

Specifically, the connection member 46 includes a connection rod 461 and an extension rod 462. The connection rod 461 has a receiving hole 4611 and a rotation preventing hole 4612. The receiving hole 4611 and the rotation preventing hole 4612 intercommunicate with each other in an axial direction and respectively extend through two ends of the connection rod 461. The rotation preventing hole 4612 has non-circular cross sections, and the second handle 44 is detachably engaged in the rotation preventing hole 4612. The extension rod 462 is connected to an outer periphery of the connection rod 461 and is coupled to the first handle 43. In assembly, the connection rod 461 is aligned with the engagement hole 454 of the second casing part 45b, and the receiving hole 4611 receives the force receiving end E of the torque meter 42. The extension rod 462 extends away from the forearm support 3.

Figure 11:
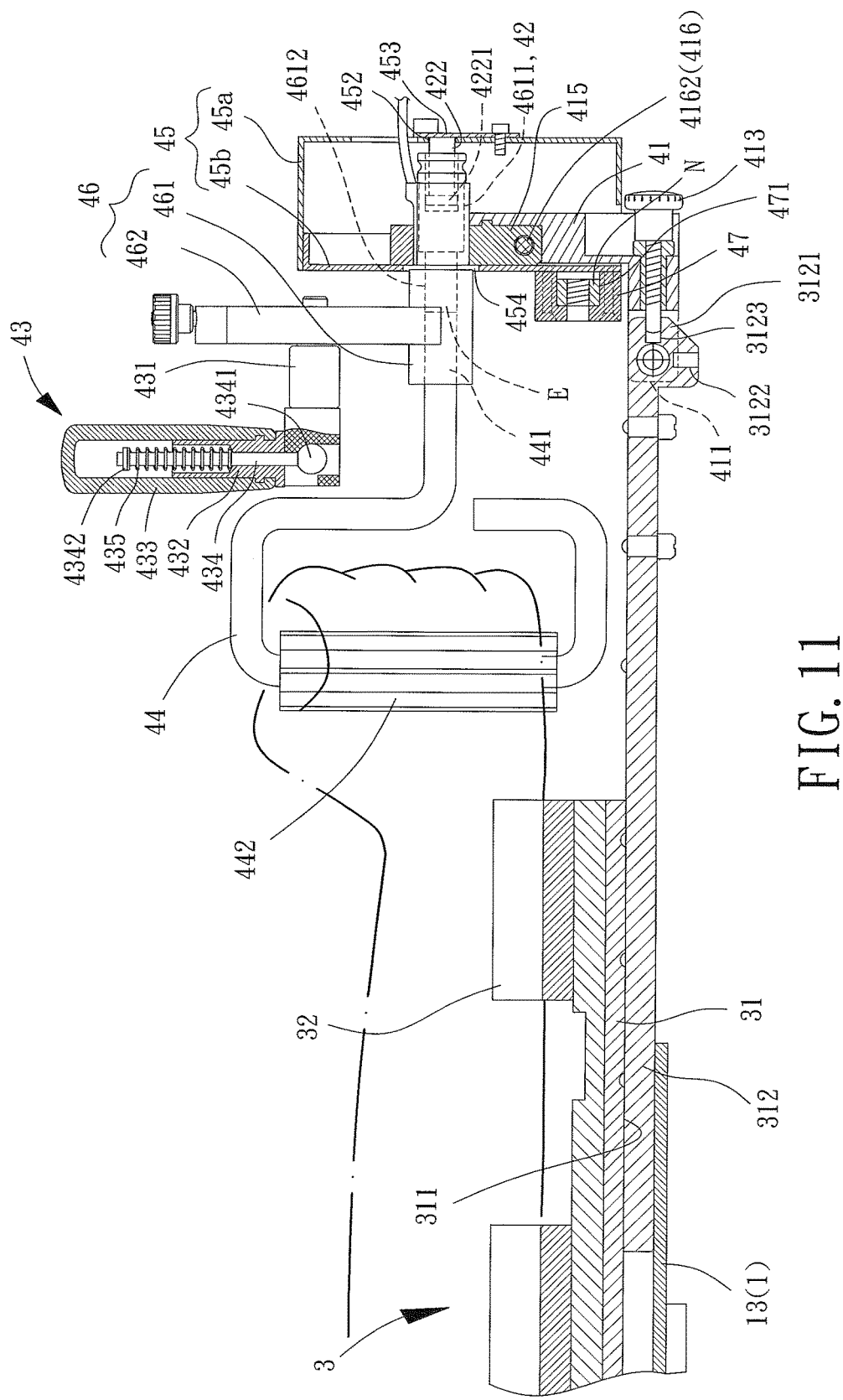
FIG. 11 is a cross sectional view of the wrist joint performance measuring device of the embodiment according to the present invention in a state for measuring the pronation torque or the supination torque of a wrist joint.

With reference to FIGS. 4 and 6, the first handle 43 includes a fixing rod 431, a follower 432, a sleeve 433, an inner rod 434, and a return spring 435. An end of the fixing rod 431 is fixed to the extension rod 462. The connection position between the fixing rod 431 and the extension rod 462 is preferably adjustable. The follower 432 is connected to the other end of the fixing rod 431. The sleeve 433 is mounted around the follower 432. The inner rod 434 extends through the follower 432 and includes an end having an arcuate surface 4341. The arcuate surface 4341 abuts an interior of the fixing rod 431. The other end of the inner rod 434 is received in the sleeve 433 and has a stopper 4342. The return spring 435 is mounted around the inner rod 434 and includes a first end abutting the follower 432 and a second end abutting the stopper 4342. Thus, the first handle 43 can be in a status in which the sleeve 433 and the fixing rod 431 are coaxial to each other (FIG. 6) or another status in which a longitudinal axis of the sleeve 433 is orthogonal to a longitudinal axis of the fixing rod 431 (FIG. 11). If it is desired to pivot the sleeve 433 relative to the fixing rod 431, the sleeve 433 is moved upwards, and the follower 432 is actuated to compress the return spring 435. Then, the sleeve 433 is pivoted to slide the arcuate surface 4341 of the inner rod 434 relative to the interior of the fixing rod 431, changing the orientation of the longitudinal axes of the inner rod 434 and the sleeve 433. When the sleeve 433 is released, the return spring 435 pushes the follower 432 back to the initial state pressing against the fixing rod 431.

Still referring to FIGS. 3 and 4, the second handle 44 includes an insertion portion 441 and a gripping portion 442. The insertion portion 441 is located on an end of the second handle 44. The insertion portion 441 is non-circular in cross section and matches with the rotation preventing hole 4612 of the connection member 46. The insertion portion 441 of the second handle 44 is inserted into the rotation preventing hole 4612 of the connection member 46. A longitudinal axis of the gripping portion 442 is orthogonal to a longitudinal axis of the insertion portion 441. Thus, the testee can hold the gripping portion 442 to easily rotate the insertion portion 441.

Furthermore, the measurement device 4 can further include a locking seat 47 and two clamping rods 48. The locking seat 47 is mounted to the second casing part 45b. The locking seat 47 includes a wider groove 471 and a narrower groove 472 intercommunicated with the wider groove 471. An end of each of the two clamping rods 48 extends through the narrower groove 472 of the locking seat 47 and is threadedly engaged with a nut "N" in the wider groove 471, tightly pressing the nut "N" against a shoulder at an intersection between the wider groove 471 and the narrower groove 472. Thus, the two clamping rods 48 can securely stand on the locking seat 47. The spacing between the two clamping rods 48 permits passage of a palm of the testee, and the two clamping rods 48 assist in positioning of the forearm of the testee at a location adjacent to the wrist, increasing the measurement accuracy. When another testee is to be tested, the two clamping rods 48 can be loosened without disengaging from the nuts "N" to permit easy adjustment of the two clamping rods 48.

Figure 5:
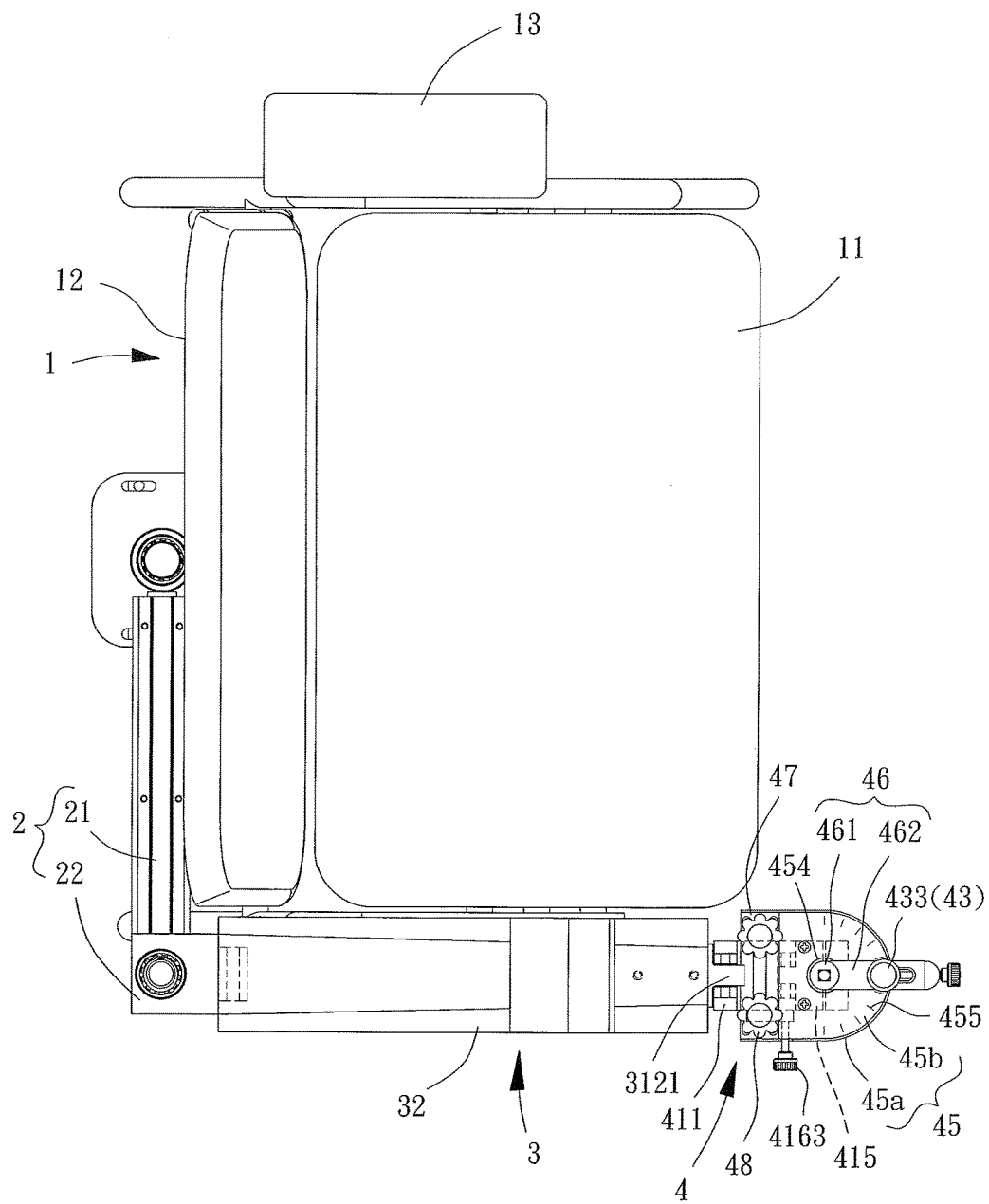
FIG. 5 is a top view of the wrist joint performance measuring device of the embodiment according to the present invention, with a forearm support positioned on the right side of a base of the wrist joint performance measuring device.

With reference to FIG. 5, according to the above structure, when it is desired to use the wrist joint performance measuring device according to the present invention to measure the performance of the wrist joint of the right hand, the switching device 2 is operated to accurately move the forearm support 3 to the right side of the seat 11 of the base 1, and the forearm support 3 is fixed on the positioning arm 13 on the right side of the base 1. Then, the relative position between the forearm support 3 and the measurement device 4 can be adjusted according to the test item.

With reference to FIG. 6, if it is desired to measure the torque and the flexion/extension movement angle of the wrist joint of the right hand, it is not necessary to mount the second handle 44 to the connection member 46. Only the first handle 43 on the connection member 46 is sufficient. Furthermore, the positioning hole 3122 of the extension arm 312 is aligned with the through-hole 412 of the pivotal seat 41, and the insert 413 extends through the through-hole 412 into the positioning hole 3122, positioning the pivotal seat 41 and the extension arm 312. In this case, the longitudinal axis of the torque meter 42 and the longitudinal axis of the sleeve 433 of the first handle 43 are substantially perpendicular to the ground.

Figure 7:
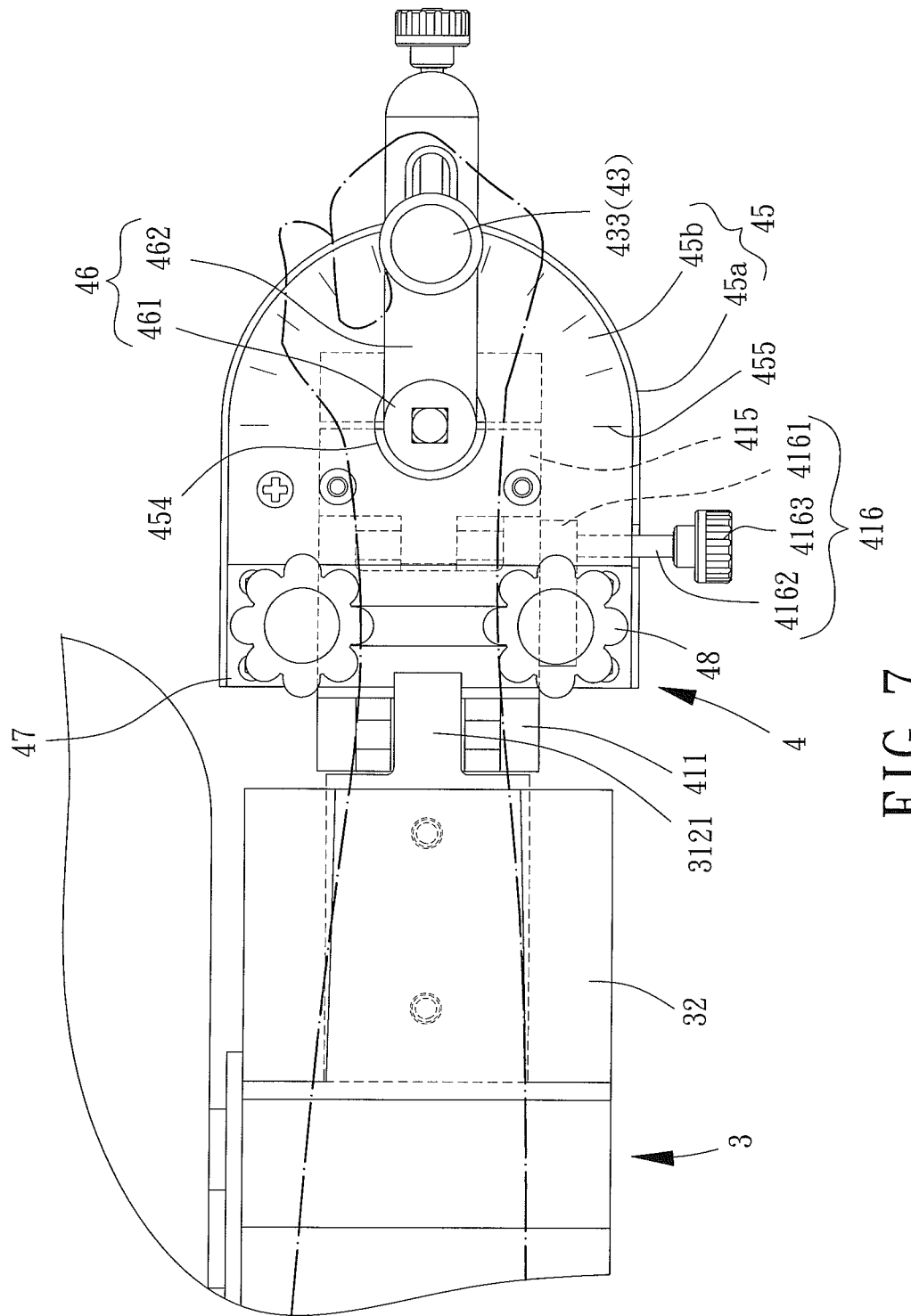
FIG. 7 is a top view of the wrist joint performance measuring device of FIG. 6.

With reference to FIGS. 6 and 7, before measurement, the extension arm 312 of the forearm support 3 is adjusted to locate the measurement device 4 in a position adjacent to the forearm support 3. The testee places the right hand on the forearm support 3 and grips the sleeve 433 of the first handle 43 with the palm. Then, an operator adjusts the spacing between the two clamping rods 48 to assist in positioning of the forearm of the testee at a position adjacent to the wrist. The fine adjustment device 416 is operated to finely adjust the position of the clamping member 415 in the compartment 414, such that the torque meter 42, the casing 45, the connection member 46, the first handle 43, the locking seat 47, and the two clamping rods 48 can be moved a small distance until the testee feels the wrist is in a relax state without applying any force. Note that if the testee has a hand that had been injured before or has a fat palm, the first handle 43 is adjusted to align with a central portion of the forearm support 3, and the wrist of the testee could be in a state requiring application of force. Thus, the fine adjustment assures the wrist of every testee is initially in a relax state without applying force, which helps in increasing the measurement accuracy in the subsequent measurement.

Before measurement of the flexion/extension torque of the wrist joint of the right hand of the rotation preventing member 422 of the torque meter 42 is pushed into the rotation prevention hole 421, and the stop plate 453 abuts the end of the rotation preventing member 422 to stop rotation of the core of the torque meter 42.

When the measurement starts, the testee holds the sleeve 433 with the palm and applies a force intending to push the first handle 43. Since the core of the torque meter 42 is fixed, the testee cannot really rotate the sleeve 433 of the first handle 43. Instead, the force is transmitted through the first handle 43 and the connection member 46 to the force receiving end "E" of the torque meter 42. Thus, the torque meter 42 can measure the flexion torque of the wrist joint of the right hand of the testee. On the other hand, if it is desired to measure the extension torque of the wrist joint of the right hand of the testee, the testee abuts the sleeve 433 of the first handle 43 with the back of the hand and applies a force, which can be appreciated by a person having ordinary skill in the art.

With reference to FIG. 8, if it is desired to measure the flexion/extension movement angle of the wrist joint of the right hand of the testee, the stop plate 453 is pivoted away, and the rotation preventing member 422 moves out of the rotation prevention hole 421 to permit rotation of the core of the torque meter 42. Thus, the first handle 43 and the connection member 46 can rotate easily about the longitudinal axis of the connection rod 461.

Figure 9:
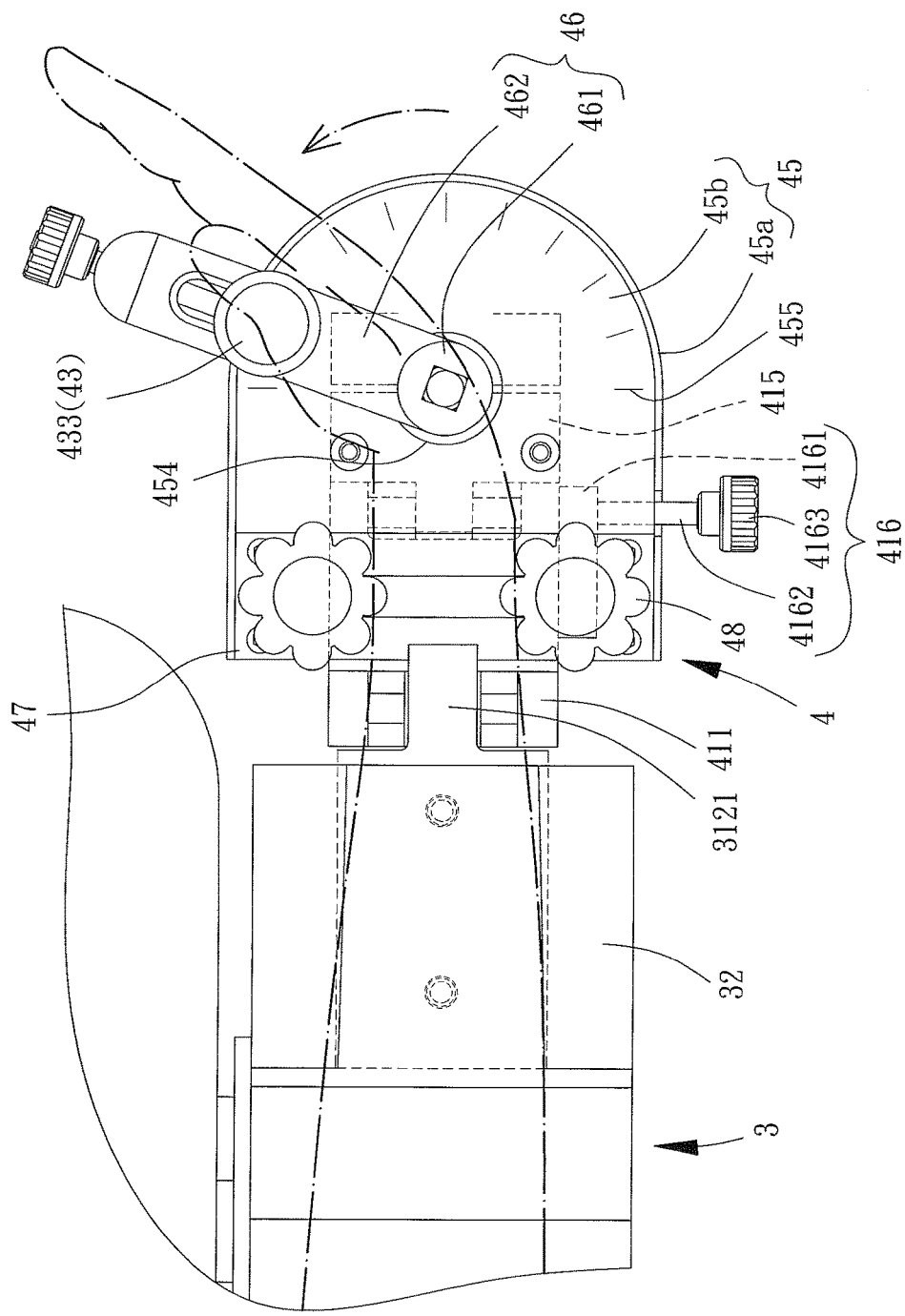
FIG. 9 is a top view of the wrist joint performance measuring device of FIG. 8, illustrating the flexion movement angle of the wrist joint.
Figure 10:
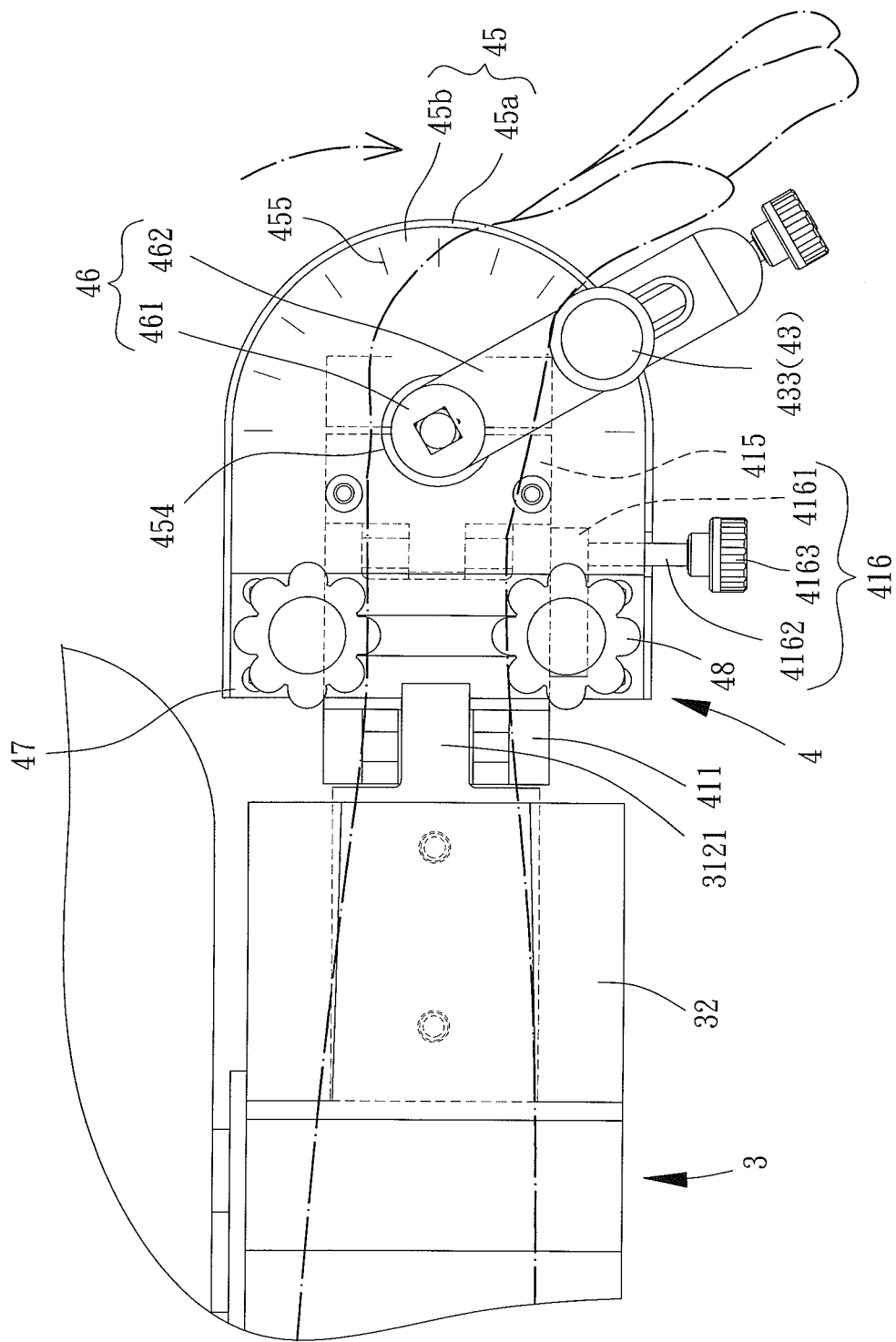
FIG. 10 is a top view of the wrist joint performance measuring device of FIG. 8, illustrating the extension movement angle of the wrist joint.

With reference to FIG. 9, specifically, the testee can hold the first handle 43 with the palm and move the first handle 43 to rotate in the counterclockwise direction, and the flexion movement angle of the wrist joint of the right hand can be known from the scale 455 on the second casing 45b of the casing 45. Alternatively, as shown in FIG. 10, the testee can rotate the first handle 43 in the clockwise direction with the back of the hand, and the extension movement angle of the wrist joint of the right hand can be known from the scale 455 on the second casing 45b of the casing 45.

With reference to FIG. 11, if it is desired to measure the torque and the movement angle of pronation/supination of the wrist joint of the right hand, the two clamping rods 48 are detached from the locking seat 47, the exposed length of the extension arm 312 outside of the guiding grove 311 is increased, and the insert 413 is moved out of the positioning hole 3122. Thus, the casing 45 and the associated elements can pivot relative to the forearm support 3 to a position in which the positioning hole 3123 of the extension arm 312 aligns with the through-hole 412 of the pivotal seat 41. The insert 413 is then inserted into the positioning hole 3123 to position the pivotal seat 41 and the extension arm 312 again. In this case, the longitudinal axis of the torque meter 42 is parallel to the ground.

An upward force and a rotational force are applied to the sleeve 433 of the first handle 43 in sequence. The longitudinal axis of the first handle 43 is converted to be orthogonal to the longitudinal axis of the fixing rod 431, permitting the insertion portion 441 of the second handle 44 to be inserted into the rotation prevention hole 4612 of the connection member 46. Next, the operator can readjust the extension arm 312 of the forearm support 3, permitting the testee to hold the gripping portion 442 of the second handle 44 by the palm after the forearm of the right hand of the testee is placed on the forearm support 3. If the testee feels that the wrist is in a state applying a force, the fine adjustment module 416 can be used to adjust the position of the clamping member 415 in the compartment 414 until the testee feels the wrist is in a relax state without applying any force.

Before measurement of the pronation/supination torque, the rotation preventing member 422 of the torque meter 42 is inserted into the rotation prevention hole 421, and the stop plate 453 abuts the end of the rotation prevention member 422 to stop rotation of the core of the torque meter 42.

When measurement starts, the testee holds the gripping portion 442 of the second handle 44 by the palm and applies a force intending to rotate the gripping portion 442 in the counterclockwise direction. Since the core of the torque meter 42 is fixed, the testee cannot really rotate the second handle 44. Instead, the force is transmitted through the second handle 44 and the connection member 46 to the force receiving end "E" of the torque meter 42, and the torque meter 42 measures the pronation torque of the wrist joint of the right hand. On the other hand, if it is desired to measure the supination torque of the wrist joint of the right hand, the testee applies a force intending to rotate the gripping portion 442 in the clockwise direction, which can be appreciated by a person having ordinary skill in the art.

Figure 12:
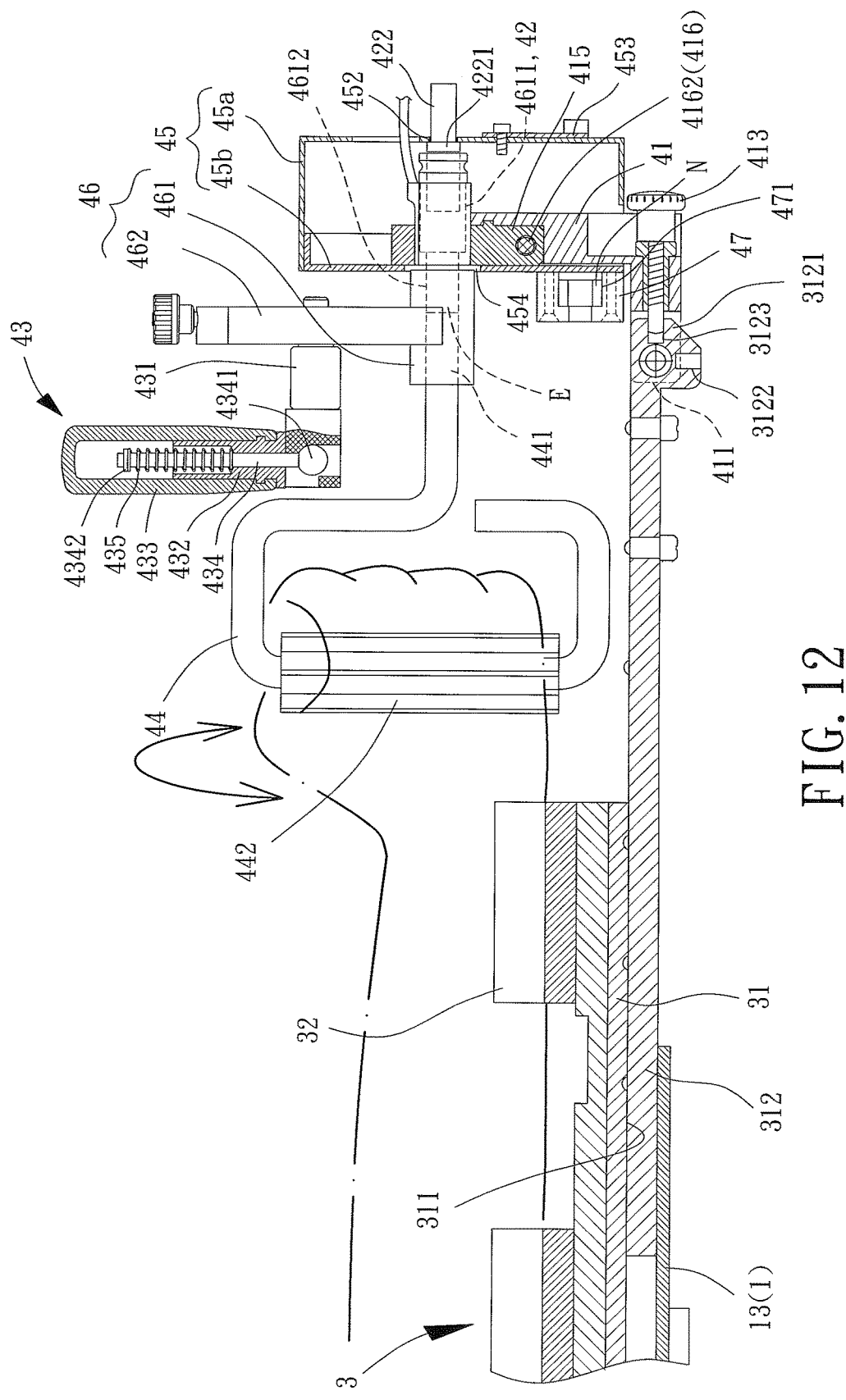
FIG. 12 is a cross sectional view of the wrist joint performance measuring device of the embodiment according to the present invention in a state for measuring the pronation/supination movement angle of a wrist joint.

With reference to FIG. 12, when it is desired to measure the pronation/supination movement angle, the stop plate 453 is pivoted away, and the rotation preventing member 422 moves out of the rotation prevention hole 421 to permit rotation of the core of the torque meter 42. Thus, the second handle 44 and the connection member 46 can rotate easily about the longitudinal axis of the connection rod 461.

Thus, the testee can hold the gripping portion 442 of the second handle 44 with the palm and rotate the second handle 44 in the counterclockwise direction, and the pronation movement angle of the wrist joint of the right hand can be known from the scale 455 on the second casing 45b of the casing 45. Alternatively, the testee can rotate the second handle 44 in the clockwise direction, and the supination movement angle of the wrist joint of the right hand can be known from the scale 455 on the second casing 45b of the casing 45.

Figure 13:
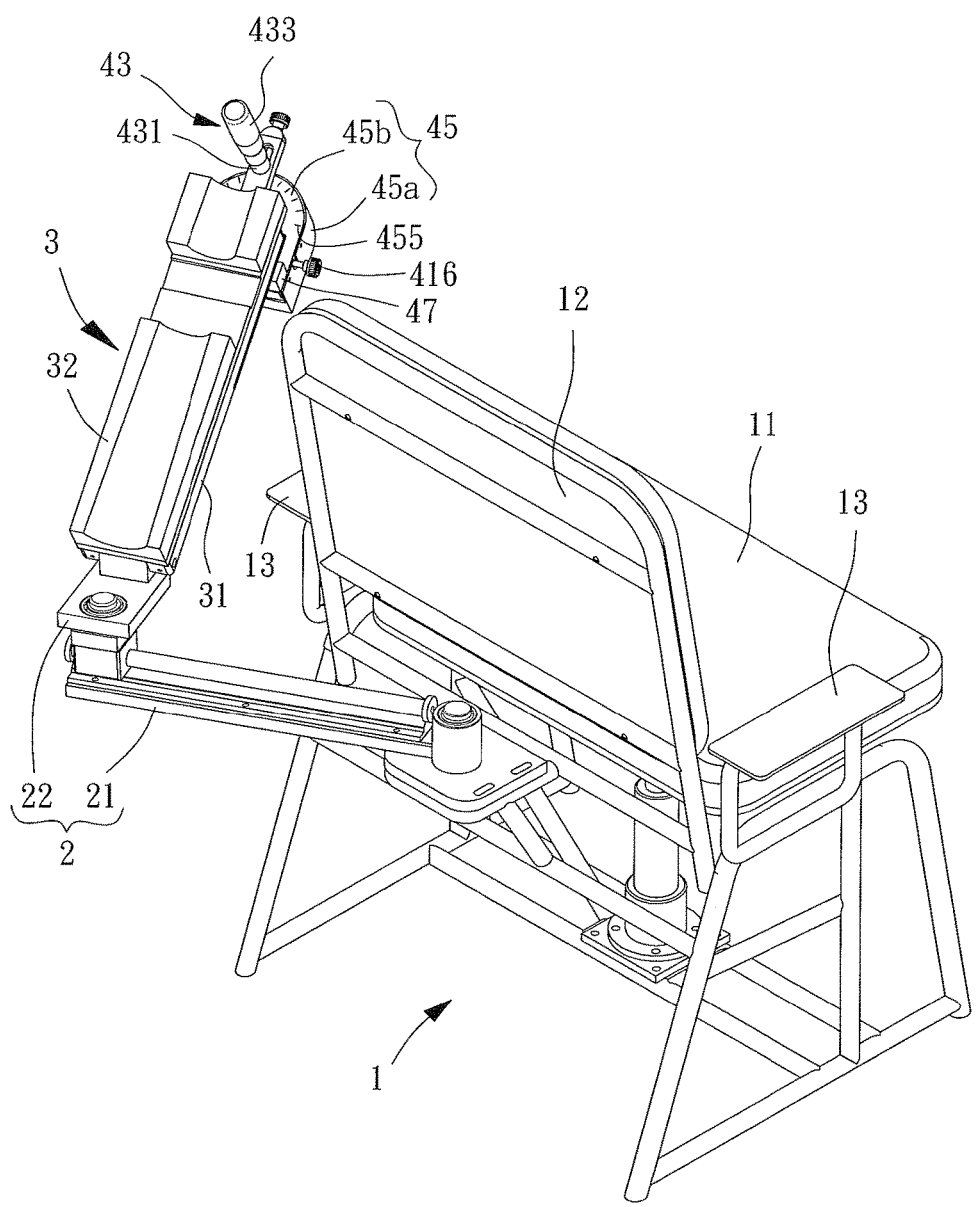
FIG. 13 is a perspective view of the wrist joint performance measuring device of the embodiment according to the present invention, with the forearm support positioned on the left side of the base of the wrist joint performance measuring device.
Figure 14:
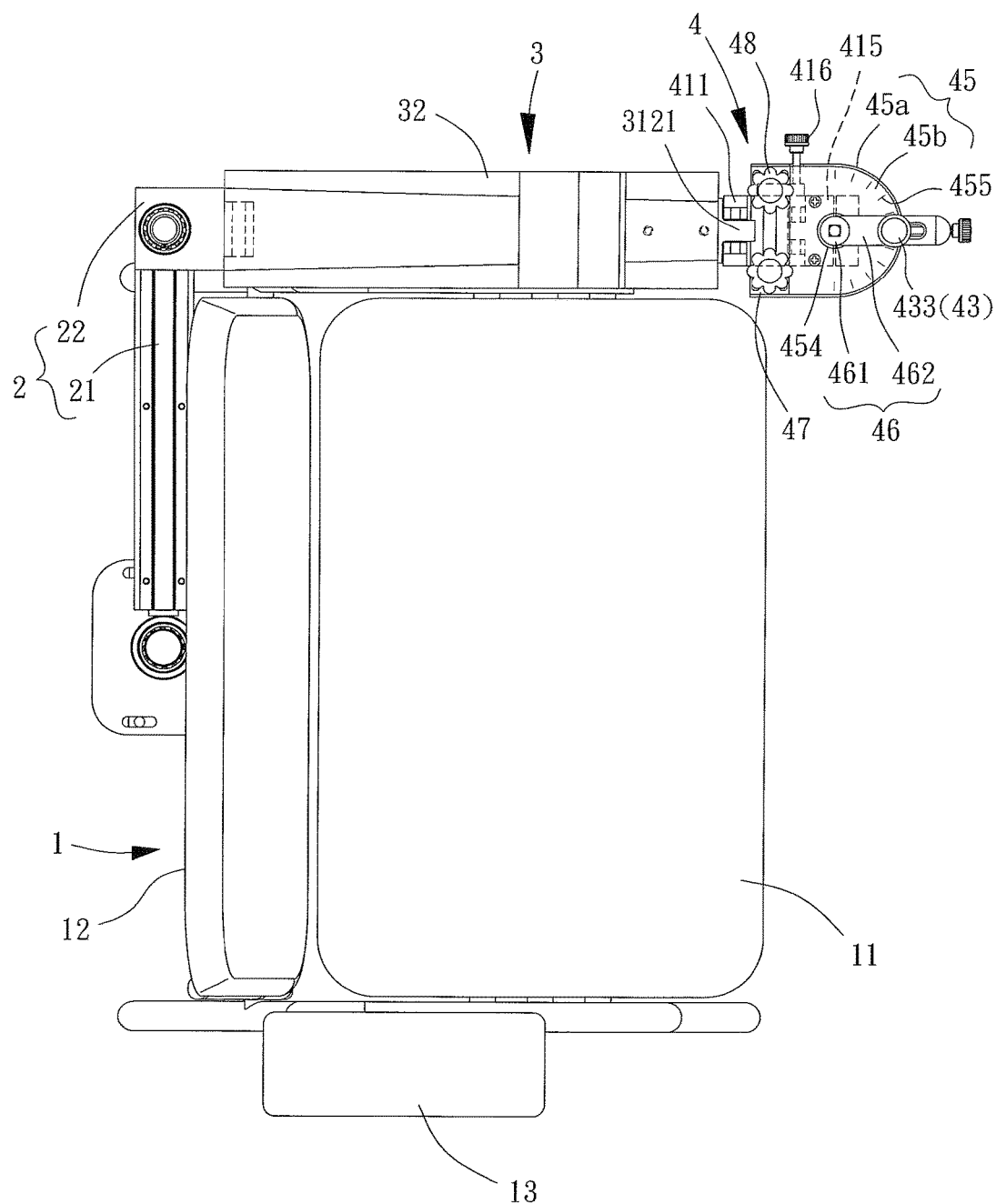
FIG. 14 is a top view of the wrist joint performance measuring device of FIG. 13.

With reference to FIGS. 13 and 14, when it is desired to use the wrist joint performance measuring device according to the present invention to measure the performance of the wrist joint of the left hand, the switching device 2 is operated to accurately move the forearm support 3 to the left side of the seat 11 of the base 1, and the forearm support 3 is fixed on the positioning arm 13 on the left side of the base 1. Then, the relative position between the forearm support 3 and the measurement device 4 can be adjusted according to the test item. The operation for measuring the torque and the movement angle of flexion/extension of the wrist joint of the left hand and the operation for measuring the torque and the movement angle of pronation/supination of the wrist joint of the left hand are substantially the same as those in the case for measuring the performance of the wrist joint of the right hand, and the detailed description is not set forth to avoid redundancy. Note that since the bottom board 31 of the forearm support 3 is pivotably connected to the second arm 22 of the switching device 2, during the switching procedure, the operator can firstly move the forearm support 3 upwards from the positioning arm 13, use the switching device 2 to move the forearm support 3 to the left side of the testee, and move the forearm support 3 downwards to the other positioning arm 13. The switching operation is intuitive to the operator to increase the operational convenience and the operational efficiency.

In view of the foregoing, the wrist joint performance measuring device according to the present invention can help the testee to accurately apply the force from the wrist to increase the measurement accuracy. Furthermore, during the procedure of changing the test item, the wrist joint performance measuring device is moved to accommodate the testee, such that the testee does not have to move while proceeding with various wrist joint performance measurements, increasing the use convenience and increasing the measurement accuracy.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A wrist joint performance measuring device comprising:
    a base including a seat and two positioning arms on two sides of the seat;
    a switching device pivotably mounted to the base;
    a forearm support connected to the switching device; and
    a measurement device including a pivotal seat, a torque meter, a first handle, and a second handle, with the pivotal seat pivotably connected to the forearm support, with the torque meter mounted to the pivotal seat, with the first handle or the second handle connected to a force receiving end of the torque meter, with the pivotal seat including a compartment, a clamping member, and a fine adjustment module, with the torque meter clamped by the clamping member, with the clamping member received in the compartment, and with the fine adjustment module configured to adjust a position of the clamping member in the compartment, wherein the forearm support and the measurement device are movable by the switching device to one of the two positioning arms and are positioned by the one of the two positioning arms.

2. The wrist joint performance measuring device as claimed in claim 1, with the forearm support including a bottom board and a forearm positioning portion, with the bottom board connected to the switching device, and with the forearm positioning portion mounted on top of the bottom board.

3. The wrist joint performance measuring device as claimed in claim 2, with the bottom board including a guiding groove and an extension arm movably received in the guiding groove, with the extension arm including an end located outside of the guiding groove, with the end of the extension arm having a pivotal portion, and with the pivotal seat including a pivotal portion pivotably connected to the pivotal portion of the extension arm.

4. The wrist joint performance measuring device as claimed in claim 3, with the extension arm including two positioning holes, with the pivotal seat including a through-hole and an insert, with the through-hole of the pivotal seat aligned with one of the two positioning holes, and with the insert extending through the through-hole into one of the two positioning holes.

5. The wrist joint performance measuring device as claimed in claim 2, with the switching device including a first arm and a second arm, with the first arm pivotably mounted to the base, with the second arm directly or indirectly connected to the first arm and pivotable relative to the first arm, and with the bottom board connected to the second arm.

6. The wrist joint performance measuring device as claimed in claim 5, wherein the bottom board is pivotably connected to the second arm.

7. The wrist joint performance measuring device as claimed in claim 5, wherein the second arm is translateably connected to the first arm.

8. The wrist joint performance measuring device as claimed in claim 1, with the clamping member including a screw hole, with the fine adjustment module including a pressing block, a threaded rod, and a knob, with the pressing block mounted to a side of the pivotal seat, with the threaded rod extending through the pivotal seat, with a threaded portion of the threaded rod received in the compartment and threadedly engaged with the screw hole of the clamping member, and with the knob mounted to an end of the threaded rod outside of the pressing block.

9. The wrist joint performance measuring device as claimed in claim 1, with the measurement device connected to the force receiving end of the torque meter by a connection member, with the first handle mounted to the connection member, and with the second handle detachably mounted to the connection member.

10. The wrist joint performance measuring device as claimed in claim 9, with the connection member including a connection rod, with the connection rod having a receiving hole and a rotation preventing hole, with the receiving hole and the rotation preventing hole intercommunicating with each other and respectively extending through two ends of the connection rod, with the force receiving end of the torque meter received in the receiving hole of the connection rod, with the rotation preventing hole having non-circular cross sections, and with the second handle detachably engaged in the rotation preventing hole.

11. The wrist joint performance measuring device as claimed in claim 10, with the second handle including an insertion portion and a gripping portion, with the insertion portion located on an end of the second handle and having a longitudinal axis, with the insertion portion matching with the rotation preventing hole, with the insertion portion of the second handle inserted into the rotation preventing hole, and with the gripping portion having a longitudinal axis orthogonal to the longitudinal axis of the insertion portion.

12. The wrist joint performance measuring device as claimed in claim 10, with the connection member further including an extension rod connected to an outer periphery of the connection rod, with the extension rod extending away from the forearm support, and with the first handle mounted to the extension rod.

13. The wrist joint performance measuring device as claimed in claim 12, with the first handle including:
- a fixing rod having an end fixed to the extension rod;
- a follower connected to another end of the fixing rod;
- a sleeve mounted around the follower;
- an inner rod extending through the follower and including an end having an arcuate surface, with the arcuate surface abutting an interior of the fixing rod, and with the inner rod further including another end received in the sleeve and having a stopper; and
- a return spring mounted around the inner rod and including a first end abutting the follower and a second end abutting the stopper.

14. The wrist joint performance measuring device as claimed in claim 10, with the measurement device further including a casing, with the torque meter received in the casing, with the torque meter including a bottom having a rotation prevention hole and a rotation preventing member, with the rotation preventing member matching with the rotation prevention hole of the torque meter and having non-circular cross sections.

15. The wrist joint performance measuring device as claimed in claim 14, with the casing including a first casing part and a second casing part coupled with the first casing part, with the first casing part including a hole, with the first casing part further including a stop plate pivotably mounted to an outer periphery of the first casing part, with the rotation preventing member extending into the rotation prevention hole, and with the stop plate blocking the hole to abut an end of the rotation preventing member.

16. The wrist joint performance measuring device as claimed in claim 15, with the rotation preventing member including an outer periphery having a protrusion, with the protrusion having a maximum width larger than a maximum diameter of the rotation prevention hole, wherein when the rotation preventing member is moved out of the rotation prevention hole, the rotation preventing member moves through the hole and partially extends out of the first casing part, and the protrusion prevents the rotation preventing member from falling out of the casing.

17. The wrist joint performance measuring device as claimed in claim 15, with the second casing part mounted to the clamping member, with the second casing part including an engagement hole, with the force receiving end of the torque meter extending out of the engagement hole, and with the connection rod of the connection member aligned with the engagement hole.

18. The wrist joint performance measuring device as claimed in claim 17, with the second casing part including an outer periphery having a scale, and with the scale provided around the engagement hole.

19. The wrist joint performance measuring device as claimed in claim 17, with the measurement device further including a locking seat and two clamping rods, with the locking seat mounted to the second casing part, with the locking seat including a wider groove and a narrower groove intercommunicated with the wider groove, and with each of the two clamping rods having an end extending through the narrower groove and threadedly engaged with a nut in the wider groove.

* * * * *